United States Patent [19]
Kampe et al.

[11] Patent Number: 5,294,375
[45] Date of Patent: Mar. 15, 1994

[54] THERMOCHROMIC MATERIALS

[75] Inventors: Marcis M. Kampe, Brookline; David P. Waller, Lexington; David C. Whritenour, Franklin, all of Mass.

[73] Assignee: Polaroid Corporation, Cambridge, Mass.

[21] Appl. No.: 747,643

[22] Filed: Aug. 20, 1991

[51] Int. Cl.$^5$ .................. G02F 1/00; C07D 333/50; C07D 333/62; C07D 305/14
[52] U.S. Cl. .................... 252/583; 549/41; 549/51; 549/52; 549/265
[58] Field of Search ............ 549/265, 41, 51, 52; 252/583, 586

[56] References Cited

U.S. PATENT DOCUMENTS

| | | | |
|---|---|---|---|
| 4,567,019 | 1/1986 | Lawton | 422/57 |
| 4,820,840 | 4/1989 | Ikegama | 549/265 |
| 4,886,733 | 12/1989 | Simon | 430/221 |

FOREIGN PATENT DOCUMENTS

| | | |
|---|---|---|
| 1-311078 | 12/1989 | Japan. |
| 615112 | 7/1978 | U.S.S.R. |
| 1363870 | 8/1984 | United Kingdom. |

OTHER PUBLICATIONS

Day, J. H., Chem. Revs., 63, pp. 65-80 (1963).
Sabongi, G. J., Chemical Triggering, Reactions of Potential Utility in Industrial Processes, Ch. 5, pp. 240-278 (1987).
Wolfers, O. S., Fiber Optic Chemical Sensors and Biosensors, vol. 2, CRC Press, Ch. 15, pp. 154-161 (1991).
Kazakova, Chemical Abstracts, 89:148275b, vol. 89, 1978.

Primary Examiner—Philip Tucker
Attorney, Agent, or Firm—Carol A. Loeschorn

[57] ABSTRACT

Disclosed is a class of bridged phthalides and sulfinate esters which exhibit reversible thermochromism. At room temperature and in the presence of base, these compounds are substantially colorless but upon the application of heat they become colored, reverting to their original colorless or weakly colored state upon cooling. This colorless to colored, temperature-dependent cycle can be repeated many times. These compounds have utility as temperature sensors and as thermal pH indicators.

18 Claims, 4 Drawing Sheets

THERMOCHROMIC MATERIALS

BACKGROUND OF THE INVENTION

(1) Field of the Invention

The present invention relates to novel chemical compounds, and more specifically, it relates to a new class of compounds which, in the presence of base, exhibit color upon the application of heat and a reversion to the original substantially colorless state upon cooling.

(2) Description of the Related Art

A number of compounds which undergo a change in color upon the application of heat and a reversion to their original color upon cooling are known in the art. This reversible, thermal triggering of a color change is called thermochromism. Examples of such compounds include spiropyrans, ethylenic compounds, e.g., dixanthylene, bianthrone, and xanthylideneanthrone, and disulfides, e.g., diphenyldisulfide and β-dinaphthyldisulfide. For a review of thermochromism and thermochromic compounds reference can be made to, for example, Sabongi, G. J., *Chemical Triggering, Reactions of Potential Utility in Industrial Processes*, Ch. 5, pp. 240 to 278 (1987); and Day, J. H., *Chem. Rev.*, 63, 65 (1963).

U.S Pat. No. 4,567,019 discloses 3,3'-bis(p-aminophenyl)phthalides which behave as thermochromes in the presence of certain organic acids. This thermochromic behavior is suspected to be the result of a temperature dependent hydrogen bonding equilibrium between one of the amine radicals of the phthalide and the —OH or —SH group of the acid.

SUMMARY OF THE INVENTION

The present invention provides novel bridged phthalides and sulfinate esters which in the presence of base act as thermochromes.

It is the primary object of the present invention to provide novel thermochromic materials.

It is another object of the present invention to provide bridged phthalides useful as temperature sensors.

It is a further object of the present invention to provide novel compounds.

Other objects of this invention will in part be obvious and will in part appear hereinafter.

The invention accordingly comprises the processes involving the several steps and the relation and order of one or more of such steps with respect to each of the others, and the products and compositions possessing the features, properties and the relation of elements which are exemplified in the following detailed disclosure, and the scope of the application of which will be indicated in the claims.

According to the present invention, it has been discovered that when certain bridged phthalides and sulfinate esters, which possess at least two phenolic hydroxy groups, one each in the 3 and 6 position of the fluorene moiety, are substituted in a particular manner in the 7'-position of the phthalide or sulfinate ester moiety, the resulting compounds are substantially colorless at room temperature but become colored on heating in the presence of base at a pH at or above the pKa of the bridged phthalide or sulfinate ester.

It will be appreciated that such thermochromic materials will find wide utility as temperature sensors. For example, the thermochromic materials of this invention are useful as visual temperature indicators, e.g., in chemical processes and in the storage of packaged temperature sensitive products. Additionally, based on their absorbance in the infrared region (defined as the region falling between approximately 700 nm and 1500 nm) the thermochromic materials of this invention can be used in conjunction with infrared diode lasers as part of a temperature monitoring system. Furthermore, the thermochromic materials of this invention are useful as thermal pH indicators.

For a fuller understanding of the nature and objects of the invention, reference should be had to the following detailed description taken in conjunction with the accompanying drawings.

DETAILED DESCRIPTION OF THE INVENTION

Figure 1:
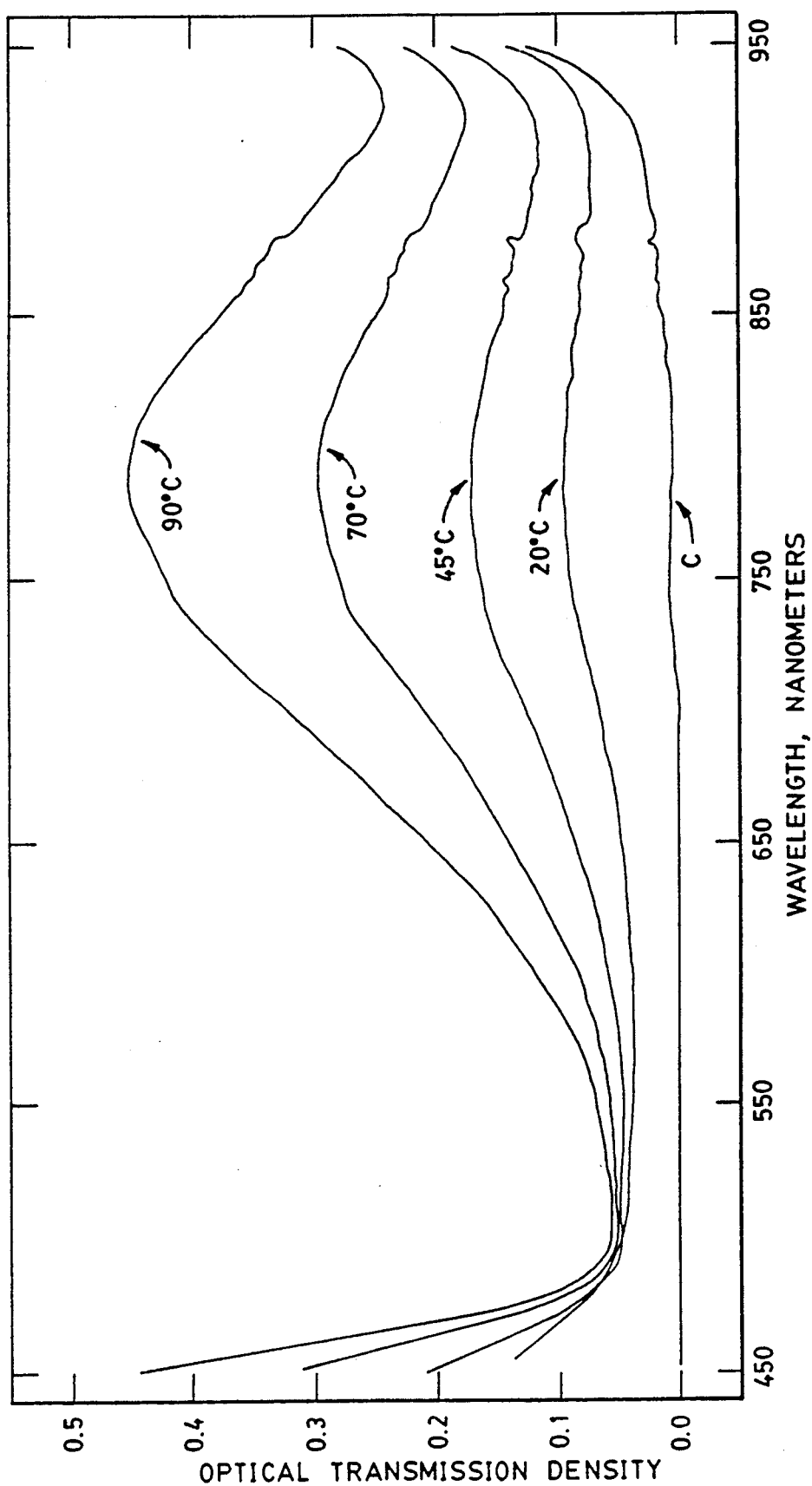
FIG. 1 is a graphic illustration of the spectral absorption characteristics of the compound of Example 3, spiro[3,6-dihydroxyfluorene-7'-methyl-9,1'-phthalan]-3'-one, in a 1.0N aqueous potassium hydroxide solution over the wavelength range of 450 to 950 nm at various temperatures. Curve C represents the optical transmission density of a control solution of 1.0N aqueous potassium hydroxide at 20° C.

The compounds of the present invention all contain the thermochromic system represented by Formula I:

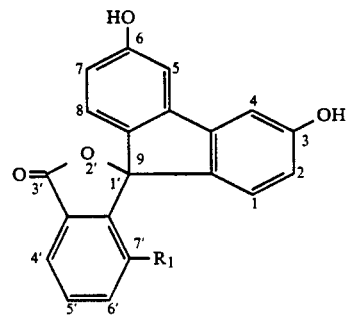

or

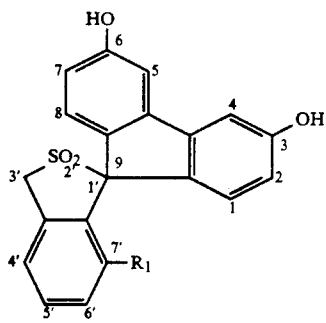

wherein $R_1$ represents a group which exerts a steric influence such that the lactone or sulfone, at a pH at or above its pKa, remains closed at room temperature but upon the application of heat overcomes said steric influence so that ring opening and hence color formation occurs. Typical $R_1$ groups include substituted or unsubstituted alkyl, aryl or alkoxy, or together with a group substituted in the 6'-position of the phthalide or sulfinate ester moiety represents the atoms necessary to complete a substituted or unsubstituted 5- or 6-membered carbocyclic ring.

The presence of a group in the 7'-position imparts increased base stability to the bridged compounds relative to those bridged compounds without a group in the 7'-position.

Compounds which exhibit color in base at room temperature when the phthalide or sulfinate ester moiety is substituted in the 7'-position are those wherein the group substituted in the 7'-position is not large enough to exert sufficient steric influence to keep the lactone or sulfone closed, e.g., when such group is a hydrogen, or when the compound is substituted in such a way that the group in the 7'-position is held sufficiently rigid so that there is insufficient steric interference with ring opening. Examples of compounds substituted in the 7'-position which exhibit color at room temperature include:

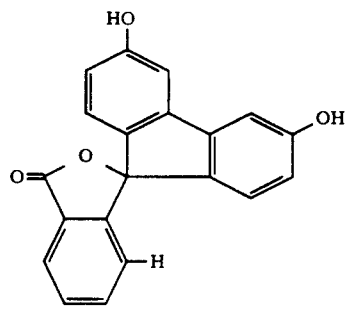

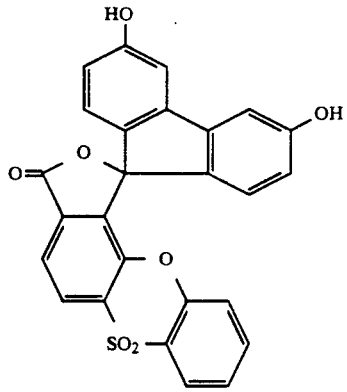

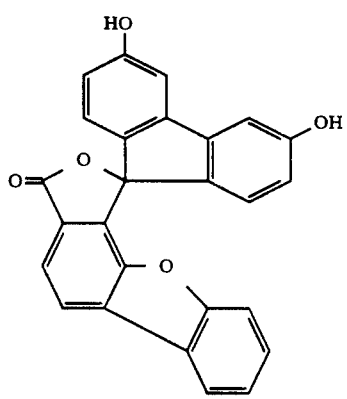

When certain groups, e.g. bromine or carboxy, are substituted in the 7'-position, the compounds are colored at room temperature which color intensifies upon the application of heat. Presumably these groups exert some steric interference at room temperature so that an equilibrium exists between the closed and opened form. These compounds behave as normal pH-dependent indicator dyes at room temperature and also as thermochromic compounds. They are disclosed and claimed in the copending U.S. patent application of M. M. Kampe, M. S. Simon, D. P. Waller, and D. C. Whritenour, Ser. No. 07/747,807, concurrently herewith.

The bridged phthalides and sulfinate esters represented by Formula I may contain substituents other than those specified. Certain groups may be added to increase or decrease the pKa of the bridged phthalide and thus enable one to vary the pH range in which the thermochromic material operates. For example, carboxy groups may be added to the 2- and 7-positions of the fluorene moiety to increase the pKa, or halogens may be placed in those same positions to decrease the pKa. Substituents may be chosen such that the temperature range to be monitored may be varied, e.g., by choice of the group for substitution in the 7'-position of the phthalide or sulfinate ester moiety.

Other substituents could be added provided they do not interfere sterically or otherwise with the thermochromic function of the bridged phthalides or sulfinate esters. Typical substituents include branched or straight chain alkyl, such as methyl, ethyl, isopropyl, t-butyl, octyl, hexadecyl, and eicosanyl; aryl, such as, phenyl and naphthyl; alkaryl, such as, tolyl, ethylphenyl, and p-dodecylphenyl; aralkyl, such as benzyl, phenethyl, and phenylhexyl; alkoxy, such as, methoxy, ethoxy, butoxy, 1-ethoxy-2-(β-ethoxyethoxy)benzyloxy, and octadecyloxy; aryloxy, such as, phenoxy and naphthoxy; alkoxyalkyl, such as, methoxyethyl, ethoxyethoxyethyl and dodecyloxyethyl; halo, such as, fluoro, bromo and chloro; sulfo; carboxy; and hydroxy. Such substituents may be substituted on one or both of the bridged fluorene rings and/or on the aryl ring of the phthalide or sulfinate ester moiety.

Furthermore, the additional substituents may comprise a fused ring, e.g., as noted above, the aryl ring of the phthalide or sulfinate ester moiety may contain as a substituent, a cycloaliphatic or an aromatic ring usually having 5 or 6 members, carbocyclic or heterocyclic and substituted or unsubstituted, bonded to adjacent carbon atoms, e.g.,

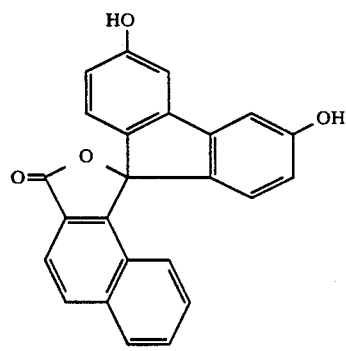

and

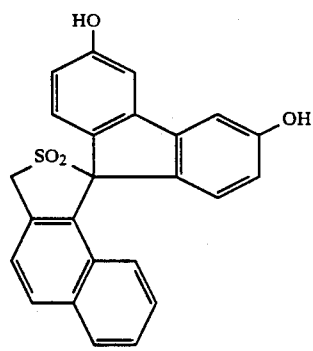

Based on steric considerations, a preferred embodiment of the compounds of this invention is represented by either of the following formula

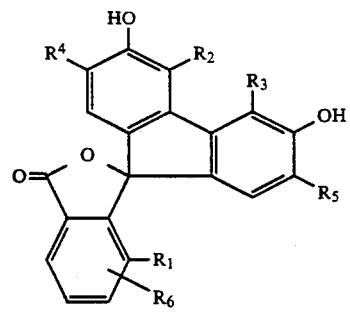

or

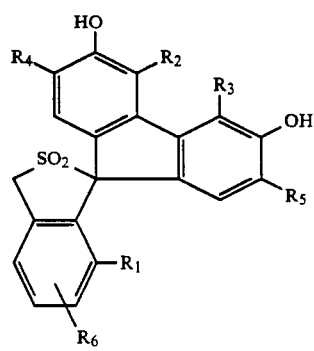

wherein $R_1$ is as defined above and $R_2$, $R_3$, $R_4$, $R_5$ and $R_6$ each independently represents hydrogen, substituted or unsubstituted alkyl, aryl or alkoxy, halo, carboxy or hydroxy, provided further that at least one of $R_2$ and $R_3$ is hydrogen.

When one of the above defined $R_1$ groups is present in the 7'-position of the phthalide or sulfinate ester moiety, the compounds of this invention are thermochromic at a pH at or above their respective pKa. However, if an $R_1$ group as defined above is not present in the 7'-position, the corresponding bridged phthalides and sulfinate esters exhibit color in base without the necessity of heat. They behave as normal pH-dependent indicator dyes as disclosed and claimed in the copending U.S. patent application of M. M. Kampe, M. S. Simon, D. P. Waller, and D. C. Whritenour, Ser. No. 07/747,807, filed concurrently herewith. As noted above, some of these compounds also exhibit thermochromism, i.e. their color intensifies upon the application of heat.

An explanation for this difference is that in the absence of an $R_1$ group in the 7'-position of the phthalide or sulfinate ester moiety, ionization and ring-opening of the lactone and sulfone occur simultaneously, at the appropriate pH, to generate color.

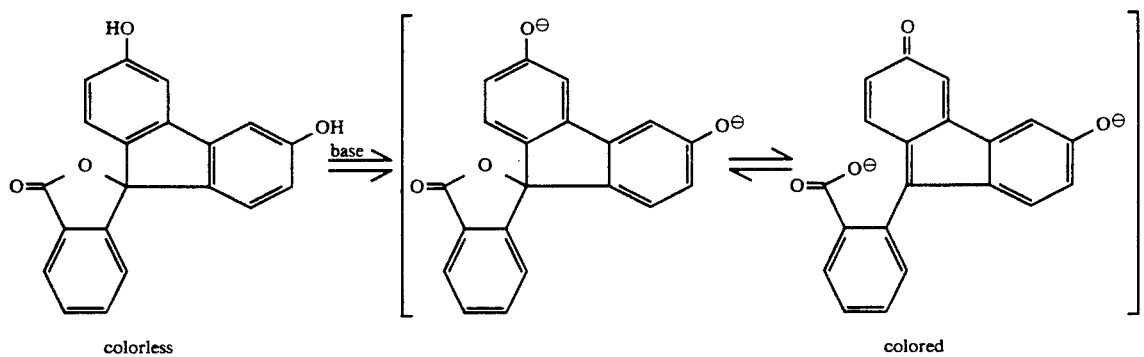

colorless     colored

However, the presence of an $R_1$ group in the 7'-position exerts an added steric influence such that initial ionization and ring opening are not synchronous but require heat to induce the lactone to open and thereby generate color.

-continued (2)

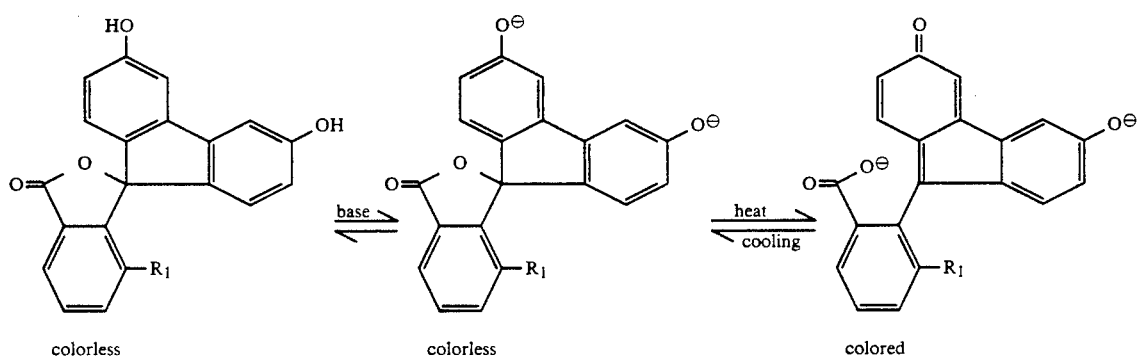

colorless     colorless     colored

As noted above, the bridged phthalides and sulfinate esters as represented in the above formulae may contain additional substituents as may be desired which do not interfere with the function of the thermal indicator for its selected ultimate use.

Specific examples of bridged phthalides within the scope of the present invention include:

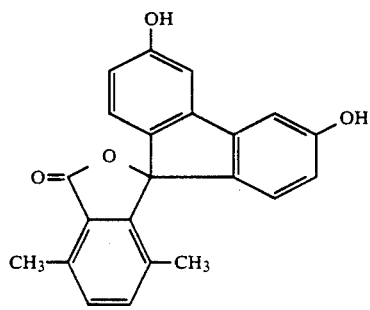

(1)

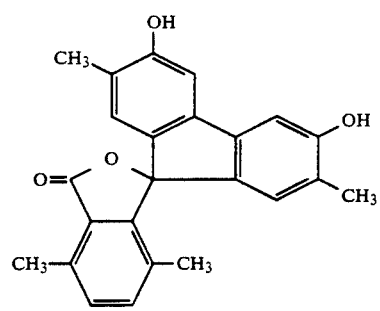

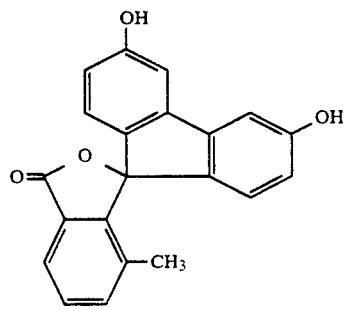

(3)

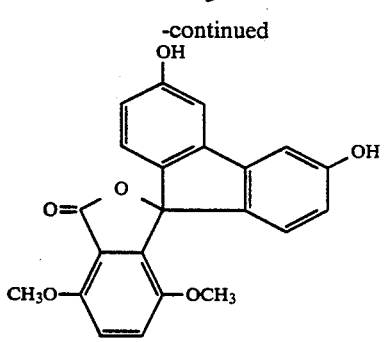
(4)

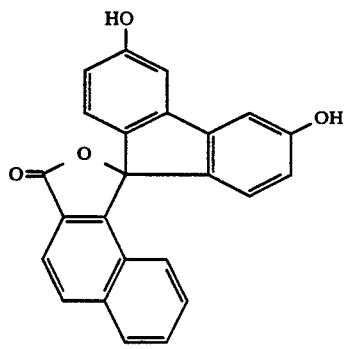
(5)

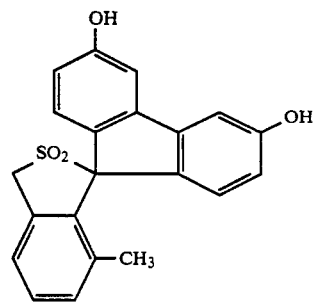
(6)

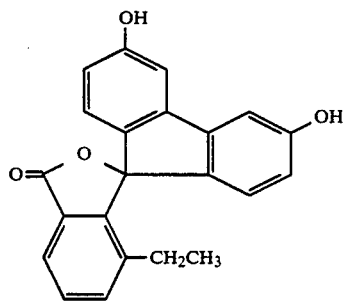
(7)

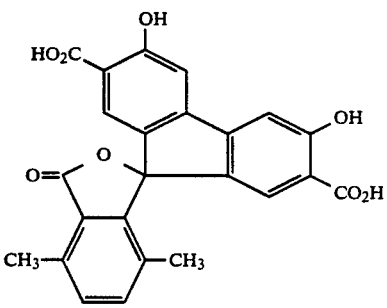
(8)

Various methods may be employed in preparing the bridged phthalides described above. One method of preparation is to react the appropriate 2,2'-dilithio-5,5'-dimethoxy biphenyl with the appropriate substituted phthalic anhydride at a reduced temperature, isolating the product, and demethylating the methyl ethers by reaction with borontribromide to yield the desired bridged phthalide.

Alternatively, the phenols could be protected by conversion to the benzyl ethers instead of the methyl ethers with subsequent deprotection proceeding in trifluoracetic acid, or by protection of the phenols with tert-butyldimethylsilane (TBDMS) and deprotecting with acetic acid/hydrochloric acid.

Another method of preparing the bridged phthalides of this invention comprises reacting the appropriate 2,2'-dilithio-5,5'-dimethoxybiphenyl with the appropriate phthalide substituted in the 7 position at a reduced temperature. The isolated product is then oxidized with potassium permanganate and the methyl ethers demethylated by reaction with borontribromide to yield the desired bridged phthalide.

Alternatively, the phenols may be protected by using any other suitable means for protecting phenols as suggested, for example, in Greene, T. W., *Protective Groups In Organic Synthesis*, John Wiley & Sons, N.Y., Chs. 2 & 3, (1981) pp. 14–107.

A further method for preparing the bridged phthalides of this invention involves the addition of an appropriately substituted ortho-metallated amido arene to an appropriately substituted flourenone. The substituted fluorenones can be prepared by either an acid catalyzed intramolecular cyclization of the appropriate ortho-biarylcarboxylic acid or by an intramolecular nucleophilic addition to a suitably substituted carboxyl derivative under basic conditions.

The following examples are given to further illustrate the present invention and are not intended to limit the scope thereof. The wavelength at which each of the compounds absorbed the maximum amount of energy (hereinafter "λmax"), reported for each of the examples below, was measured in 1.0N alkali solution.

EXAMPLE 1

Preparation of spiro[3,6-dihydroxyfluorene-4',7'-dimethyl-9,1'-phthalan]-3'-one having the formula

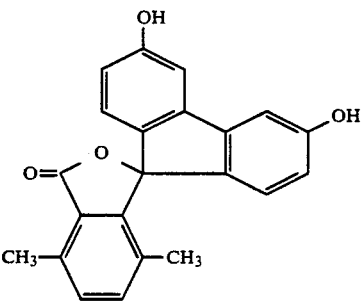

(1) 37.02 g of N-bromosuccinimide dissolved in 165 ml of dimethylformamide was added dropwise, over a one-hour period, to a cooled (−5° C.) solution of 22.3 g of 3,3'-dimethoxybiphenyl in 60 ml of dimethylformamide. The resulting solution was stirred at room temperature overnight. The solution was poured onto crushed ice, and additional ice cold water was added to obtain a white precipitate. The white precipitate was filtered, washed with warm water, dried in vacuo for 2¼ hours, washed with boiling hexanes and dried overnight under vacuum to yield 27 g of 2,2'-dibromo-5,5'-dimethoxybiphenyl.

(2) 5.58 g of 2,2'-dibromo-5,5'-dimethoxybiphenyl was dissolved in 65 ml of tetrahydrofuran under an atmosphere of nitrogen. The resulting solution was cooled to −25° C. and 20 ml of 2.5M n-butyllithium in hexanes was added. A white slurry formed which was stirred at −25° C. for thirty minutes and then allowed to come to room temperature and kept there until a clear solution resulted. The reaction mixture was cooled again in an ice-bath. 3.52 g of 3,6-dimethylphthalic anhydride was introduced and the reaction was allowed to come to room temperature over a 2-hour period and was then refluxed under nitrogen for 2¼ hours. After reflux, the reaction mixture was cooled in an ice-bath and quenched with a saturated ammonium chloride solution. This was further diluted with ethyl ether and the organic layer was separated, dried over anhydrous magnesium sulfate, filtered and concentrated to yield a tacky mass. This was washed with hot hexanes and recrystallized from 65 ml of acetonitrile to yield 4.10 g of protected bridged phthalide, spiro[3,6-dimethoxyfluorene-4',7'-dimethyl-9,1'-phthalan]-3'-one, as a white solid. The structure was confirmed by infrared, NMR and mass spectroscopy.

(3) 0.35 g of spiro[3,6-dimethoxyfluorene-4',7'-dimethyl-9,1'-phthalan]-3'-one was dissolved in 50 ml of methylene chloride to obtain a clear solution. 2.5 ml of borontribromide was added, and the solution was stirred overnight at room temperature. The reaction mixture was poured onto crushed ice and concentrated under reduced pressure to remove the methylene chloride. The tan precipitate was filtered, washed with cold methylene chloride and dried in the open air to yield 0.175 g of the title compound, spiro[3,6-dihydroxyfluorene-4',7'-dimethyl-9,1'-phthalan]-3'-one, as an off-white solid. The structure was confirmed by infrared, NMR and mass spectroscopy.

When the title compound was dissolved in 1N alkali to ensure a pH greater than the pka of the title compound, the solution was substantially colorless. Upon heating to 95° C. the solution turned green (λmax=790 nm) and then reverted to colorless upon cooling to room temperature. The colorless to colored cycle was repeatable.

EXAMPLE 2

Preparation of spiro[3,6-dihydroxy-2-methylfluorene-4',7'-dimethyl-9,1'-phthalan]-3'-one having the formula

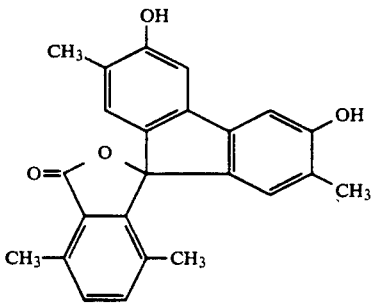

The title compound was prepared according to the procedure given in Example 1 above with 3,3'-dimethoxy-4,4'-dimethyl biphenyl being substituted in the reaction with N-bromosuccinimide. The structure was confirmed by NMR and infrared spectroscopy. A solution of the product in 1.0N potassium hydroxide (bringing the pH to a value higher than the pka of the title compound) turned green (λmax=825 nm) when heated to 95° C. and upon subsequent cooling to room temperature reverted to its original, substantially colorless state.

EXAMPLE 3

Preparation of spiro[3,6-dihydroxyfluorene-7'-methyl-9,1'-phthalan]-3'-one having the formula

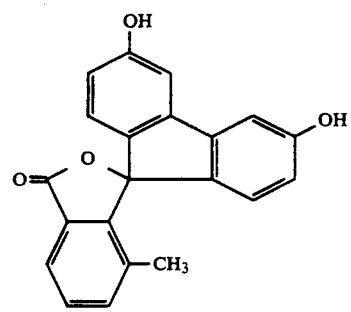

(1) 3.0 g of 2,2'-dibromo-5,5'-dimethoxy biphenyl (prepared as in Example 1 above) was dissolved in 35 ml of dry tetrahydrofuran and cooled to −25° C. To the chilled solution was added dropwise, over 10 minutes, 7.8 ml of 2.5M n-butyllithium in hexanes which had been diluted with 10 ml of tetrahydrofuran. Stirring was continued at −25° C. for 20 minutes and at room temperature for an additional 20 minutes whereupon the resulting clear, straw-colored solution was again chilled to −25° C. and 1.2 g of 7-methylphthalide (prepared according to the procedure of J. Bunnett and C. Hauser, J. Am. Chem. Soc., 87, 2214 (1965)) was added. The solids quickly dissolved and the mixture was stirred at −25° C. for 10 minutes, at room temperature for 10 minutes followed by reflux for 4 hours. After stirring at room temperature overnight, the reaction was quenched with 55 ml of a saturated ammonium chloride solution and 5 ml of concentrated hydrochloric acid. The resulting mixture was diluted with ether and the organic layer was separated, washed with dilute hydrochloric acid and with water, and dried. Concentration of the solvent yielded a tacky solid which was redissolved in ether and triturated with hexanes to give an off-white precipitate. The precipitate was filtered, dissolved in 6 ml of glacial acetic acid and refluxed for 10 minutes. The cooled reaction mixture was poured into cold water to obtain an off-white solid which was filtered and dried under vacuum to afford 1.0 g of spiro[3,6-dimethoxyfluorene-7'-methyl-9,1'-phthalan]. The structure was confirmed by NMR and mass spectroscopy.

4) To 1.0 g of spiro[3,6-dimethoxyfluorene-7'-methyl-9,1'-phthalan] dissolved in 20 ml of pyridine was added 2.0 ml of water. The resulting clear, straw-colored solution was heated to 50°-55° C., and 0.474 g of potassium permanganate was added in small portions over 4.5 hours. Each new portion was added once the purple permanganate color from the previous addition had disappeared. After the addition was completed, the precipitated solids were removed by filtration and extracted with 5 portions of hot pyridine. The combined pyridine extracts were diluted with ice water and acidified with concentrated hydrochloric acid. The resulting precipitate was filtered, washed with water and dried in vacuo to yield 0.829 g of spiro[3,6-dimethoxyfluorene-7'-methyl-9,1'-phthalan]-3'-one as a white solid. The structure was confirmed by NMR and mass spectroscopy.

5) To 0.828 g of spiro[3,6-dimethoxyfluorene-7'-methyl-9,1'-phthalan]-3'-one dissolved in 110 ml of methylene chloride was added 3.5 ml of boron tribromide and the resulting mixture was refluxed for 20 hours. The reaction was quenched by pouring into ice-water and diluted with methylene chloride. The organic layer was washed several times with water, separated, concentrated to 15 ml and diluted with 5 ml of hexanes. The resulting light tan solid was filtered, dried and dissolved in 35 ml of methanol to which were added 5 ml of water and 0.5 g of sodium bicarbonate. The resulting mixture was heated on a steam bath for 2 hours and quenched with acidic water to yield a precipitate. The precipitate was filtered, washed with water and dried in vacuo to yield 0.54 g of the title compound, spiro[3,6-dihydroxyfluorene-7'-methyl-9,1'-phthalan]-3'-one, as an off-white solid. The structure was confirmed by mass spectroscopy and infrared analysis. The title compound exhibited a thermochromic effect ($\lambda max = 790$ nm) when heated to 95° C. in the presence of 1.0N hydroxide (to attain a pH greater than the pka of the title compound) or when heated as a solid in a suitable matrix once the phenolic dianion had been formed, e.g., by absorbing the title compound onto silica, adding a solution of sodium hydroxide and allowing the mixture to dry, and placing the dried solid material in a test tube.

EXAMPLE 4

Preparation of spiro[3,6-dihydroxyfluorene-4',7'-dimethoxy-9,1'-phthalan]-3'-one having the formula

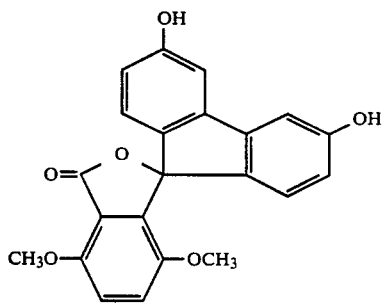

1) To 100 ml of methylene chloride was added 19.5 g of 2,2'-dibromo-5,5'-dihydroxybiphenyl, 35 ml of dihydropyran and 6 drops of phosphorous oxychloride and the resulting clear mixture was stirred at room temperature overnight. The methylene chloride was removed under reduced pressure and the remaining mixture was heated on a steam bath for 30 minutes. After all the unreacted dihydropyran was removed under vacuum, the remaining oil was extracted into hot hexanes leaving behind an oily residue. The hexanes were removed, and the resulting amber oil was dried in vacuo overnight to yield 23 g of 2,2'-dibromo-5,5'-tetrahydropyran (THP)-dihydroxybiphenyl.

2) The 2,2'-dibromo-5,5'-THP-dihydroxybiphenyl (5.12 g) was converted to 2,2'-dilithio-5,5'-THP-dihydroxybiphenyl and then reacted with 3,6-dimethoxyphthalic anhydride, as done in step 2 of Example 1 above, except that the corresponding protected bridged phthalide was not isolated. After quenching with saturated ammonium chloride and diluting with ethyl ether, 10 ml of concentrated hydrochloric acid was introduced to the rapidly stirred two phase system. The organic layer was separated, dried and concentrated. The residue was triturated with hot hexanes and the resulting tan material recrystallized from methylene chloride to yield 0.175 g of the title compound. The structure was confirmed by NMR and mass spectroscopy.

The title compound exhibited a thermochromic effect ($\lambda max = 790$) going from a substantially colorless state at room temperature to an emerald green state when heated to 95° C. in 1.0N potassium hydroxide (provides pH greater than the pka of the title compound). Upon cooling to room temperature, the thermochromic material reverted to its substantially colorless state.

EXAMPLE 5

Preparation of spiro[3,6-dihydroxyfluorene-6',7'-phenyl-9,1'-phthalan]-3'-one having the formula

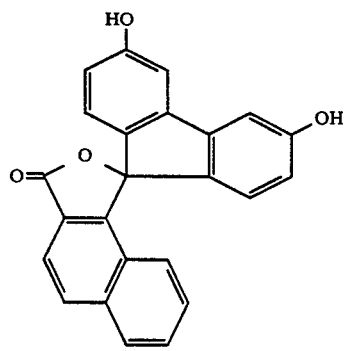

To 12 g of 2,2'-dibromo-5,5'-dimethoxybiphenyl (prepared as in Example 1, above) in 200 ml of dry tetrahydrofuran at −65° C. under an atmosphere of nitrogen was added, dropwise, a cold mixture of 87 ml of a 1.7M solution of t-butyllithium in hexane. After the addition was complete, the mixture was warmed to ~−7° C., and a solution of 6.0 g of 1-naphthalide dissolved in 110 ml of warm tetrahydrofuran was added dropwise. The resulting mixture was stirred at room temperature for 3 hours, quenched with dilute hydrochloric acid and stirred overnight. The organic layer was separated, washed with water, dried over anhydrous magnesium sulfate and concentrated to yield a tan oil. The oil was extracted with hot hexanes and then dissolved in methylene chloride and washed with a concentrated sodium bicarbonate solution to remove any unreacted starting materials. The methylene chloride solution was dried over anhydrous magnesium sulfate, treated with silica gel, filtered and concentrated to yield 1.6 g of spiro[3,6-dimethoxyfluorene-9,1'-naphthbenzoisofuran] as an off-white solid. The structure was confirmed by infrared and mass spectroscopy.

To 1.0 g of the spiro[3,6-dimethoxyfluorene-9,1'-naphthbenzoisofuran] dissolved in 18 ml of pyridine was added 2.0 ml of water. To the resulting solution was added, over 2¼ hours, 0.65 g of potassium permanganate. The mixture stood at 40° C. over the weekend and was then poured into water and made acidic with concentrated hydrochloric acid. The mixture was extracted with ethylacetate, the ethylacetate was washed with water, dried over anhydrous magnesium sulfate and concentrated to yield 1.0 g of spiro[3,6-dimethoxyfluorene-6',7'-phenyl-9,1'-phthalan]-3'-one as an off-white solid. The structure was confirmed by NMR, infrared and mass spectroscopy.

Demethylation of the methyl ethers was accomplished with borontribromide in a manner analogous to step 3 of Example 1. 0.900 g of the protected bridged phthalide yielded 0.475 g of the title compound, spiro[3,6-dihydroxyfluorene-6',7'-phenyl-9,1'-phthalan]-3'-one as an off-white solid whose structure was confirmed by NMR, infrared and mass spectroscopy.

When the title compound was dissolved in 1N potassium hydroxide to bring the pH to a value greater than the pka, a pale green color resulted. Heating to 95° C. intensified the color to an emerald green and subsequent cooling to room temperature caused the title compound to revert to its original pale green color (λmax=809).

The 1-naphthalide employed above in Example 5 was synthesized as set out below:

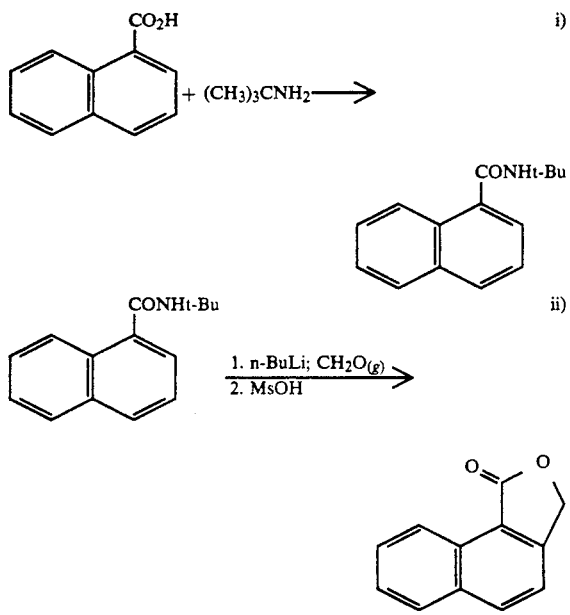

i) 10 g of 1-naphthoic acid, 50 ml of thionyl chloride and 1 drop of dimethylformamide were stirred at 25° C. for 4 hours during which time all solids had dissolved. The excess thionyl chloride was distilled via aspirator and the residual gum was diluted with 100 ml of methylene chloride. Upon cooling to 0° C., 14 ml of t-butylamine was added dropwise and the resulting solution was allowed to stir overnight. After pouring the reaction mixture into 100 ml of 5% hydrochloric acid, the organic layer was separated and the aqueous layer was extracted with methylene chloride. The organic layers were combined, dried over anhydrous magnesium sulfate, filtered and the solvent removed under vacuum. Recrystallization from acetonitrile yields 13 g of 1-t-butylnaphthalamide as white needles, m.p. 146° C.

ii) To a solution of 4 g of 1-t-butylnaphthalamide in 70 ml of tetrahydrofuran at 0° C. was added dropwise over a 5-minute period 18 ml of a 2.5N butyllithium solution in hexane (2.2 equivalents). The resulting dark brown-red solution was stirred at 0° C. for 30 minutes and then formaldehyde gas was bubbled in under a stream of nitrogen until the color had faded and the solution thickened.

The reaction was quenched with 50 ml of water and extracted with 3×60 ml of methylene chloride. The methylene chloride extracts were combined, filtered through silica, and concentrated. The residue was recrystallized from methylene chloride/hexane to yield 1.8 g of 2-hydroxymethyl-1-t-butylnaphthalamide as a white solid whose structure was confirmed by NMR.

The 2-hydroxymethyl-1-t-butylnaphthalamide was heated at 60° C. in 20 ml methanesulfonic acid for 2 hours. The mixture was poured into ice-water and the precipitated solids were collected and dried to yield 1.1 g of 1-naphthalide as an off-white solid. The structure was confirmed by NMR.

EXAMPLE 6

Preparation of spiro[3,6-dihydroxyfluorene-1,3-dihydro-2,2-dioxy-7-methylbenzoisothiophene] having the formula

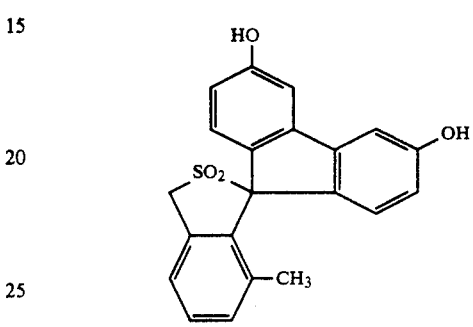

To 7.0 g of spiro[3,6-dimethoxyfluorene-7'-methyl-9,1'-phthalan] (prepared as in Example 3 above) dissolved in 275 ml of methylene chloride was added 18 ml of boron tribromide. The resulting amber/brown mixture was refluxed for 72 hours and then quenched with crushed ice. A dark precipitate formed which was collected by filtration, washed with hexanes and water and dried in vacuo for 6 hours. To the dried precipitate, suspended in 350 ml of acetone and heated on a steam bath, was slowly added 80 ml of a concentrated sodium bicarbonate solution. The resulting mixture was poured into a solution of 850 ml of water and 50 ml of concentrated hydrochloric acid. The dark blue precipitate which formed was collected by filtration, washed with water and dried in vacuo to yield 6.0 g of the bromomethyl compound represented by the following structure

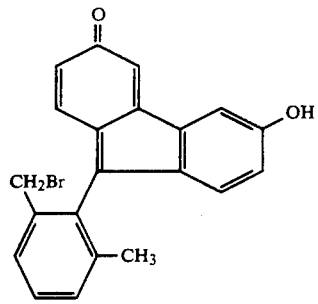

which was confirmed by NMR spectroscopy.

60 ml of methanol was saturated with sodium sulfite nonahydrate and the mixture was filtered to remove the undissolved residue. The methanol solution was then gently heated on a steam bath while adding, in small increments, a total of 1 g of the bromomethyl compound synthesized above. After stirring at room temperature overnight, the solution was poured into dilute hydrochloric acid and the resulting precipitate was filtered, washed with water and dried under vacuum to yield 0.7 g of spiro[3,6-dihydroxyfluorene-1,3-dihydro-7-methylbenzoisothiophene] as an olive gray solid.

1.9 g of potassium peroxymonosulfate (commercially available under the tradename Oxone®) was added dropwise, over a one-hour period, to a cooled (0°) solution of 0.70 g of spiro[3,6-dihydroxyfluorene-1,3-dihydro-7-methylbenzoisothiophene] in 75 ml of methanol. The cooled solution was stirred for 2 hours, 35 ml of water was added and the solution was stirred at room temperature overnight.

The mixture was poured into 250 ml of cold water and the resulting gray precipitate was filtered and washed with water. The solid was purified by dissolving in ether, treating with silica gel and Norit A, drying the ether solution and concentrating it to yield 0.22 g of spiro[3,6-dihydroxyfluorene-1,3-dihydro-2,2-dioxy-7'-methylbenzoisothiophene] as an off-white solid. The structure was confirmed by mass spectroscopy and infrared analysis.

Upon dissolving spiro[3,6-dihydroxyfluorene-1,3-dihydro-2,2-dioxy-7'-methylbenzoisothiophene] in 1N potassium hydroxide to bring the pH to a value greater than the pka of the bridged sulfone and heating to 95° C., the solution turned green ($\lambda max = 809$). Upon cooling to room temperature the solution returned to its original substantially colorless state.

As noted above, the compounds of this invention exhibit thermochromism at a pH at or above their respective pKa, which for most of the compounds of this invention falls within a pH range of 8–14.

As examples of materials useful for obtaining the necessary pH, mention may be made of the alkali metal hydroxides, for example, sodium and potassium hydroxide, other inorganic basic materials, e.g., sodium carbonate and the like, or strong organic bases, such as, t-butoxide, or quaternary ammonium bases, e.g., tetramethylammonium hydroxide and the like.

In accordance with this invention, a bridged phthalide or sulfinate ester, as defined above, is combined with a suitable base, either in solution or as a dry powder coating, such that the resulting pH is at or above the pKa of the bridged phthalide or sulfinate ester. Application of heat to the resulting substantially colorless thermochromic material causes a color change to occur which reverts to its original substantially colorless state upon cooling and can be regenerated by heating.

As mentioned above, the thermochromic materials of this invention have utility as thermal pH indicators. By heating the thermochromic material to a desired temperature, the pH change of the thermochromic material can be monitored as a function of color.

Also, as noted above, the thermochromic materials of this invention have utility as temperature sensors. The thermochromic materials are useful as visual temperature indicators, e.g., in chemical processes and in the storage of packaged temperature sensitive products. In addition to their use as visual temperature indicators, the thermochromic materials of this invention are useful as temperature monitors.

Where temperature monitoring is desired over repeated temperature cycles, the preferred thermochromic material of this invention employs a bridged phthalide. The bridged phthalide is preferred over the bridged sulfinate ester based on experimental data which indicates a decrease in color density for the bridged sulfinate esters at identical temperatures over repeated heating/cooling cycles. One possible explanation, consistent with the experimental data, could be decomposition of the bridged sulfinate ester with heating. No similar decrease in color density was seen when the thermochromic material incorporated a bridged phthalide.

One method of temperature monitoring contemplates placing the thermochromic material of this invention in a suitable cell, one that transmits light of the appropriate wavelength, or by coating it on a suitable support, one that reflects or transmits light of the appropriate wavelength, and placing it where temperature monitoring is desired. A beam of monochromatic light of the appropriate wavelength (a wavelength at which the thermochromic material absorbs light) is directed at the thermochromic material and a detector, set up to work in conjunction with the system, measures the density of the reflected or transmitted light (depending upon the cell or support chosen). An appropriate means to compare the detected density of reflected or transmitted light to a calibrated standard for the particular thermochromic material chosen is employed to ascertain the temperature. The system can additionally include a means, e.g., a bell or flashing light, as a warning that the system has reached a certain temperature and/or a means to raise or lower the temperature of the system to keep it within a predetermined temperature range and/or a means to shut off or turn on the system in response to temperature.

Most of the thermochromic materials of this invention have substantial absorbance in the infrared region of the spectrum when thermally activated so that the above described temperature monitoring system could be used with an infrared diode laser as the source of monochromatic light. Since infrared diode lasers can be made compact and small this temperature monitoring method would be particularly useful where temperature monitoring of very small systems, e.g., in the electronics industry, is desirable.

The thermochromic materials of this invention could also be used in fiber optic temperature sensors such as the device by M. Brenci, described in Otto S. Wolfbers, *Fiber Optic Chemical Sensors and Biosensors*, Vol. 2, CRC Press, Ch. 15, pp. 157–158 (1991). In such a device, the thermochromic material is encapsulated with an optical fiber to guide light from a white light source. The temperature is ascertained from the significant change in absorption characteristics of the material with temperature.

The operation of this invention may be illustrated by the following test procedures. The optical transmission density of the compound of Example 3 at a concentration of $1.46 \times 10^{-3}$M in 1.0N aqueous potassium hydroxide was measured over the wavelength range of 450 nm to 950 nm at various temperatures as shown in FIG. 1. Curve C represents the transmission density of a control solution containing 1.0N aqueous potassium hydroxide at 20° C. The solid curves 20° C., 45° C., 70° C., and 90° C. represent the transmission density of the compound of Example 3 at 20° C., 45° C., 70° C., and 90° C. respectively. The optical transmission density of spiro[3,6-dihydroxyfluorene-9,1'-phthalan]-3'-one, the compound corresponding to that of Example 3 but without the methyl group in the 7'-position, at a concentration of $1.8 \times 10^{-4}$M in 0.05N aqueous potassium t-butoxide was measured over the wavelength range of 400 to 1000 nm at 20° C. as shown in the curve in FIG. 2.

Figure 2:
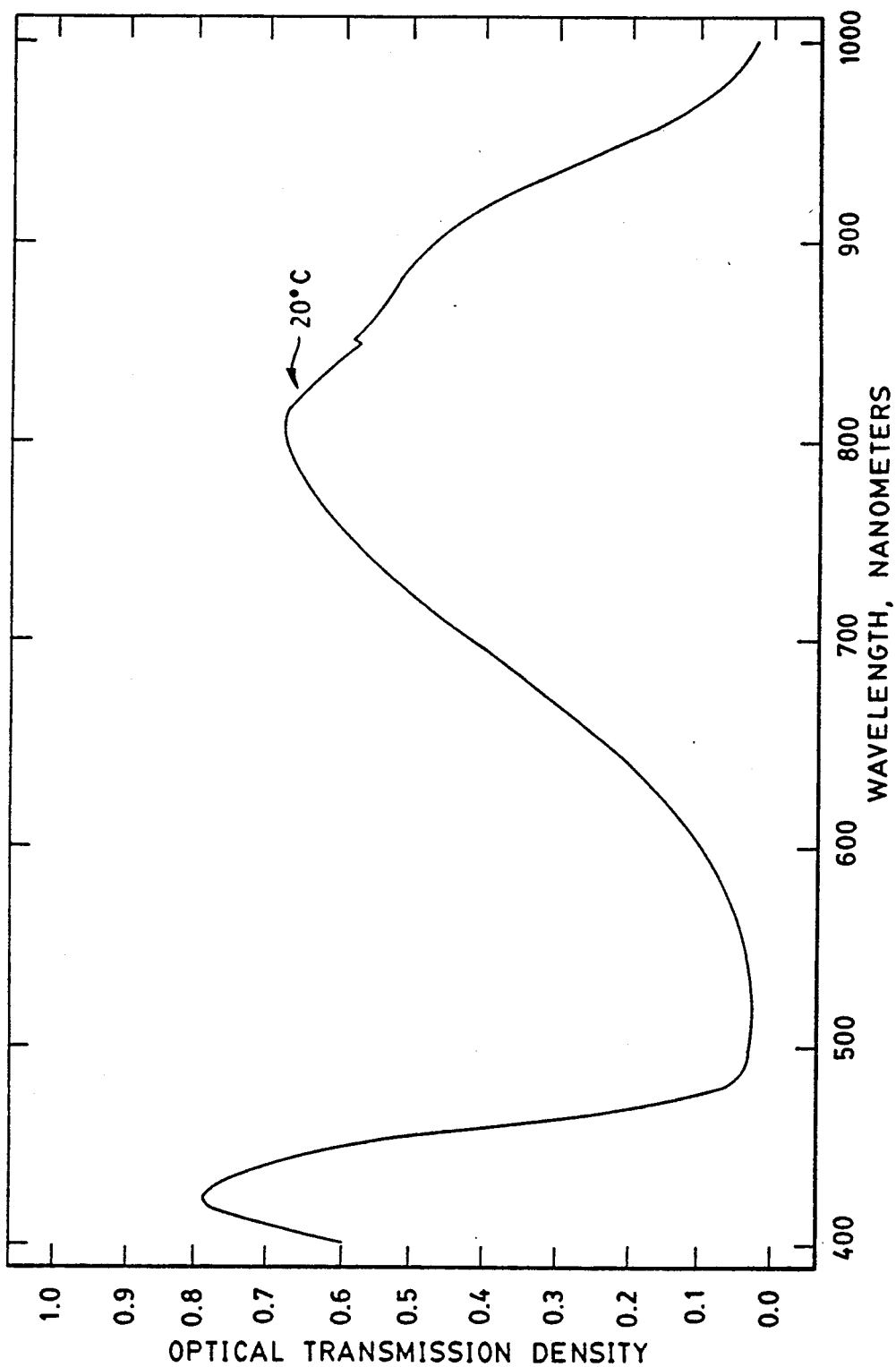
FIG. 2 is a graphic illustration of the spectral absorption characteristics of spiro[3,6-dihydroxyfluorene-9,1'-phthalan]-3'-one, the bridged phthalide corresponding to that of Example 3 but without the methyl group in the 7'-position, in 0.05N aqueous t-butoxide over the wavelength range of 400 to 1000 nm at 20° C.

As can be seen from reference to FIGS. 1 and 2, the presence of the methyl group in the 7'-position of the phthalide moiety imparts thermochromism to the compound. When the methyl group is present, as in FIG. 1, the compound requires heat to absorb light. At 20° C. there is negligible absorbance, but as the temperature increases, the amount of spiro[3,6-dihydroxy-fluorene-7'-methyl-9,1'-phthalan]-3'-one existing in the light absorbing form also increases as is evident from curves 20° C., 45° C., 70° C., and 90° C. in FIG. 1. However, when the 7'-methyl group is replaced with a hydrogen, the corresponding compound exhibits color in base at 20° C., without the necessity of heat as verified by the substantial absorbance shown by the curve in FIG. 2. The curve in FIG. 2 confirms that in the absence of a group in the 7'-position as defined by the present invention, the compounds act as regular indicator dyes in alkali.

As a further illustration of the present invention, the optical transmission density of a solution of the compound of Example 5 at a concentration of $1.47 \times 10^{-3}$M in 1.0N potassium hydroxide was measured at a first temperature of 20° C. and then upon heating at temperatures of 50° C., 70° C., 80° C., and 90° C. The resulting curves are designated curves 20° C., 50° C., 70° C., 80° C., and 90° C., respectively, in FIG. 3. The optical transmission density of the solution containing the compound of Example 5 was again measured upon cooling at temperatures of 80° C., 70° C., 50° C., and 20° C. The resulting curves are shown in FIG. 4, designated curves 80° C., 70° C., 50° C., and 20° C., respectively. Curve 90° C. in FIG. 4 represents the optical transmission density of the same solution containing the compound of Example 5 upon subsequent reheating at 90° C., and the curve designated 20° C. in FIG. 4 also represents the optical transmission density of that solution upon cooling at 20° C. The curve is essentially identical to the previously measured optical transmission density at 20° C., described above, and hence there is no discernible difference in the two curves and they appear as one.

Figure 3:
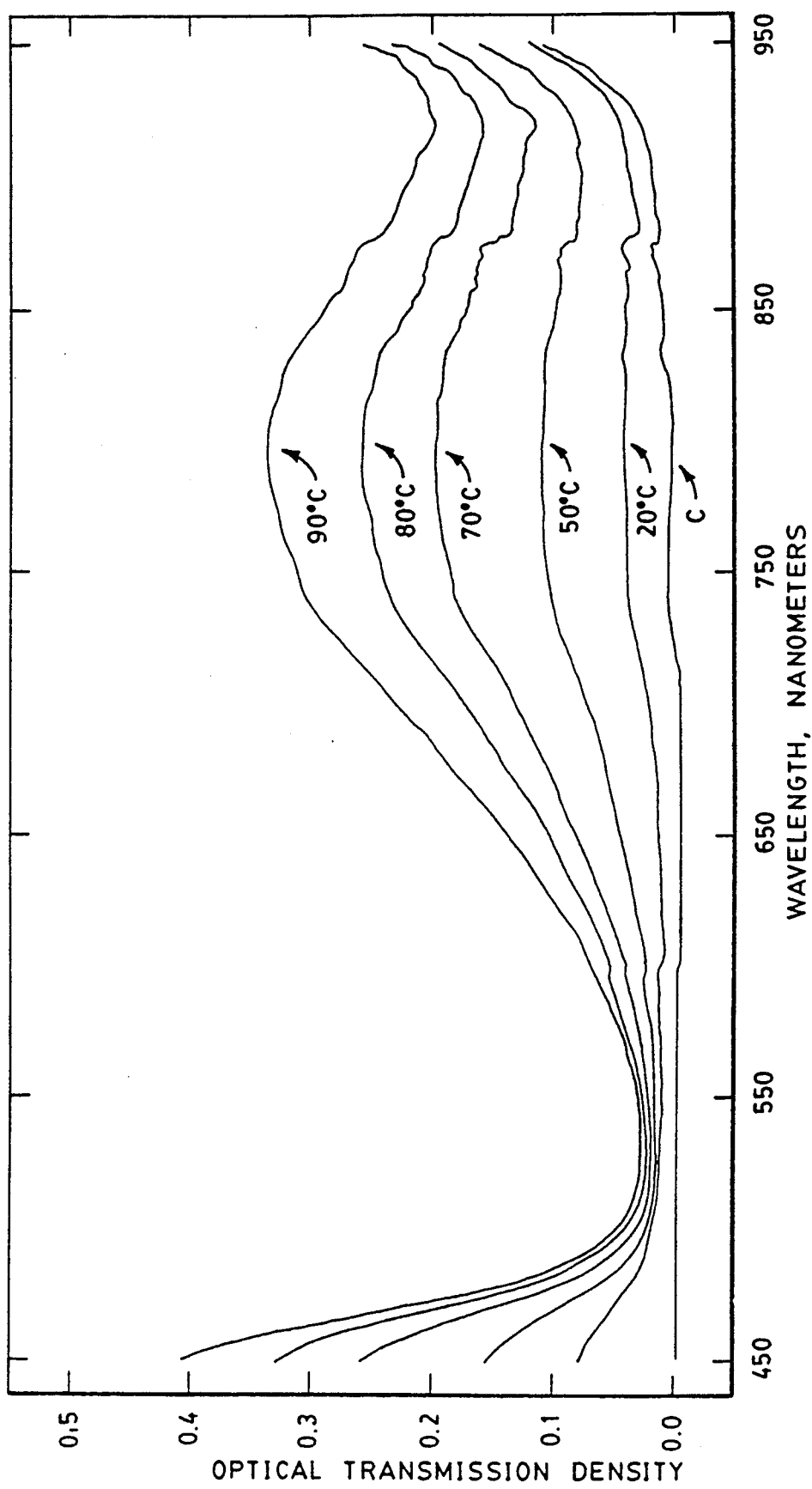
FIGS. 3 and 4 are graphic illustrations of the spectral absorption characteristics of the compound of Example 5, spiro[3,6-dihydroxyfluorene-6',7'-phenyl-9,1'-phthalan]-3'-one, in 1.0N aqueous potassium hydroxide over the wavelength range of 450 to 950 nm at various temperatures upon heating and again at those same temperatures upon cooling. Curve C in both Figures represents the optical transmission density of a control solution of 1.0N aqueous potassium hydroxide at 20° C.
Figure 4:
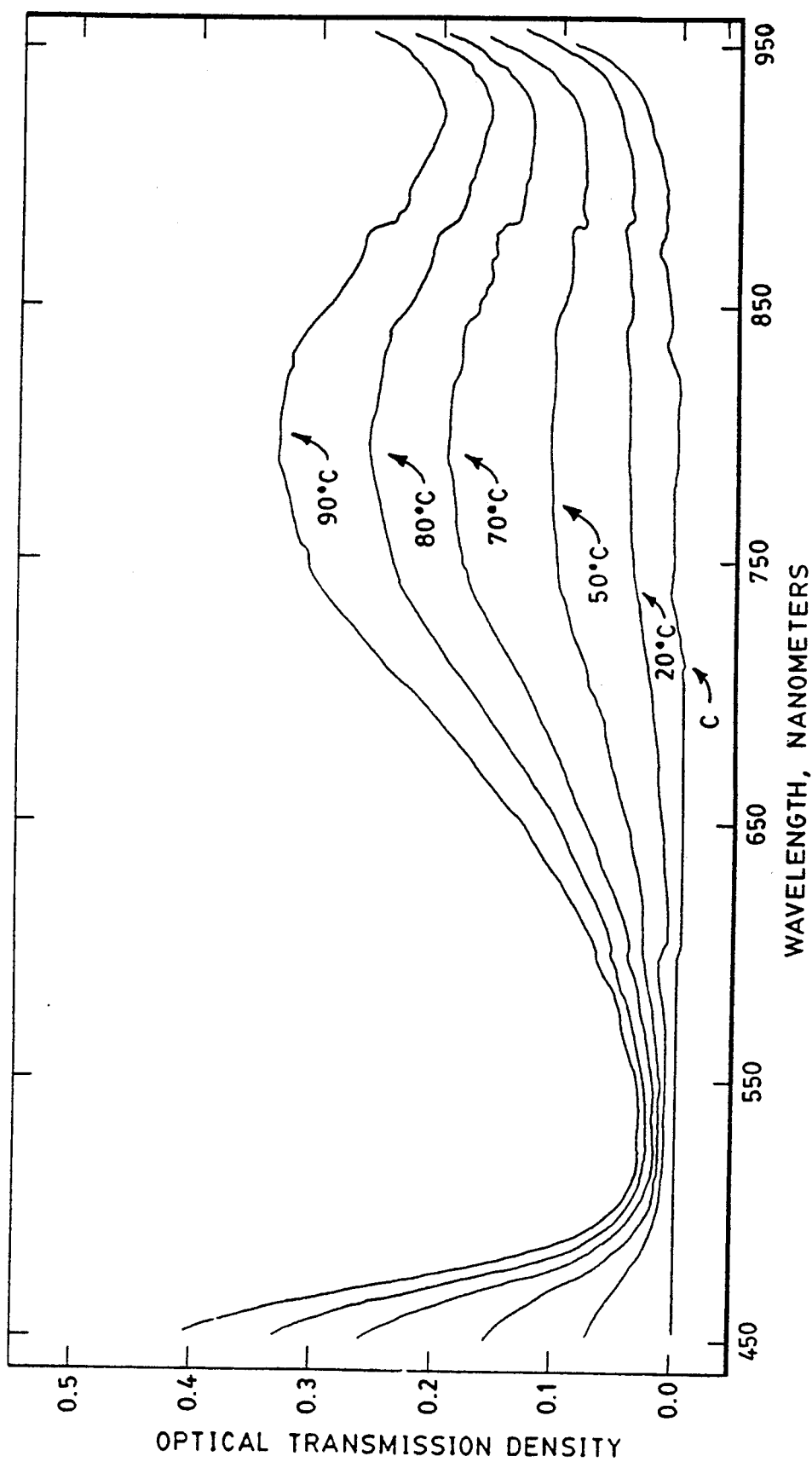

Curve C in both FIGS. 3 and 4 represents the optical transmission density of a 1.0N solution of potassium hydroxide at 20° C.

As can be seen by reference to FIGS. 3 and 4, the colorless to colored, heat dependent cycle of the bridged phthalides of this invention is repeatable. A comparison of the optical transmission for the compound of Example 5, upon heating and cooling, as represented by the optical transmission densities in FIGS. 3 and 4, is essentially the same at the same temperature during the heating and cooling cycles. Subsequent reheating to 90° C. and cooling to 20° C. gives essentially the same absorbance as measured earlier at both 20° C. and 90° C. as indicated by a comparison of curves 20° C. and 90° C. in FIGS. 3 and 4. The optical transmission density for the compound of Example 3 was measured in the same way, and it was found that the spectral curves were the same for that compound at the same temperatures over repeated heating/cooling cycles.

The temperature range which can be monitored by the thermochromic materials of the present invention is limited only by the particular bridged phthalide or sulfinate ester chosen. The greater the steric influence exerted by the substituent in the 7'-position, the higher the temperature required to overcome the barrier to ring opening of the lactone or sulfone and accordingly, the broader the temperature range in which the thermochrome could operate.

Since certain changes may be made in the above subject matter without departing from the spirit and the scope of the invention herein involved, it is intended that all matter contained in the above description and/or shown in the accompanying drawings shall be interpreted as illustrative and not in any limiting sense.

What is claimed is:

1. A thermochromic material, comprising:
   (a) a compound containing the thermochromic system represented by the formula

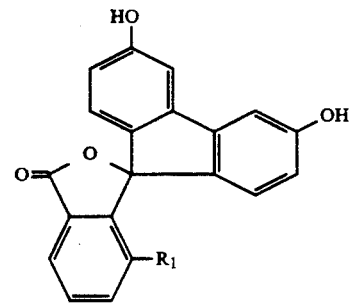

or

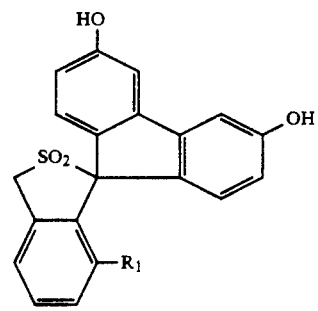

wherein $R_1$ represents a group which exerts a steric influence such that the lactone or sulfone would remain closed at room temperature but upon the application of heat would overcome said steric influence so that ring opening could occur; and (b) a basic component providing a pH at or above the pka of said compound;

said thermochromic material being characterized in that it goes from a substantially colorless state at room temperature to a more intensely colored state upon heating to an elevated temperature and returns to its substantially colorless state upon subsequent cooling to room temperature.

2. A thermochromic material as defined in claim 1 wherein $R_1$ is substituted or unsubstituted alkyl, aryl or alkoxy, or together with a group substituted in the 6'-position of the phthalide or sulfinate ester moiety represents the atoms necessary to complete a substituted or unsubstituted 5- or 6-membered carbocyclic ring.

3. A thermochromic material as defined in claim 2 wherein said compound is represented by the formula

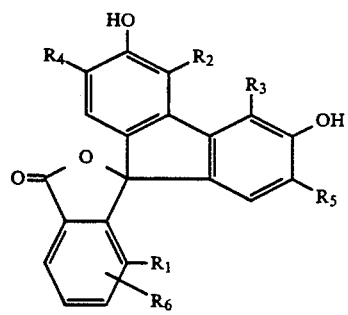

wherein $R_2$, $R_3$, $R_4$, $R_5$ and $R_6$ each independently represent hydrogen, substituted or unsubstituted alkyl, aryl or alkoxy, halo, carboxy or hydroxy, provided further that at least one of $R_2$ and $R_3$ is hydrogen.

4. A thermochromic material as defined in claim 2 wherein said compound is represented by the formula

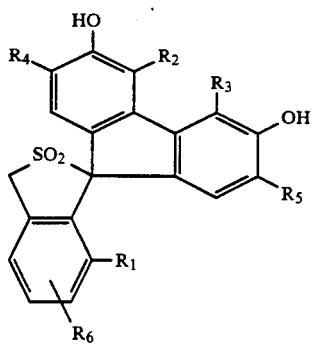

wherein $R_2$, $R_3$, $R_4$, $R_5$ and $R_6$ each independently represent hydrogen, substituted or unsubstituted alkyl, aryl or alkoxy, halo, carboxy or hydroxy, provided further that at least one of $R_2$ and $R_3$ is hydrogen.

5. A thermochromic material as defined in claim 3 wherein $R_1$ is methyl and $R_2$, $R_3$, $R_4$, $R_5$ and $R_6$ are each hydrogen.

6. A thermochromic material as defined in claim 3 wherein $R_1$ and $R_6$ are each methoxy and $R_2$, $R_3$, $R_4$ and $R_5$ are each hydrogen.

7. A thermochromic material as defined in claim 3 wherein $R_1$ and $R_6$ are each methyl, $R_2$ and $R_3$ are each hydrogen, and $R_4$ and $R_5$ are each carboxy.

8. A thermochromic material as defined in claim 3 wherein $R_1$ taken together with $R_6$ when $R_6$ is in the 6'-position of the phthalide moiety represent the atoms necessary to complete a phenyl ring and $R_2$, $R_3$, $R_4$ and $R_5$ are each hydrogen.

9. A thermochromic material as defined in claim 4 wherein $R_1$ is methyl and $R_2$, $R_3$, $R_4$, $R_5$ and $R_6$ are each hydrogen.

10. A thermochromic material as defined in claim 1 wherein the basic component is an aqueous solution of an alkali metal hydroxide.

11. A thermochromic material as defined in claim 1 wherein the basic component is an organic base.

12. A compound of the formula

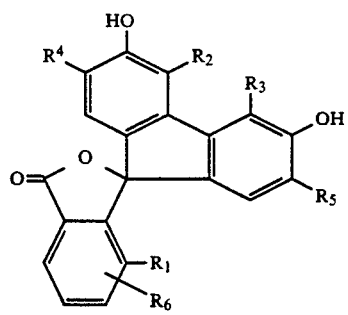

or

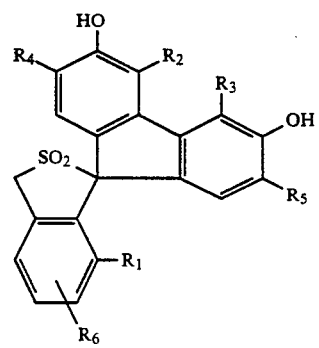

wherein $R_1$ represents a group which exerts a steric influence such that the lactone or sulfone, when said compound is at a pH at or above its pKa, remains closed at room temperature but upon the application of heat overcomes said steric influence so that ring opening and hence color formation occurs;

$R_2$, $R_3$, $R_4$, $R_5$ and $R_6$ each independently represents hydrogen, substituted or unsubstituted alkyl, substituted or unsubstituted aryl, alkoxy, halo, carboxy, or hydroxy, further providing that at least one of $R_2$ and $R_3$ are hydrogen.

13. A compound according to claim 12

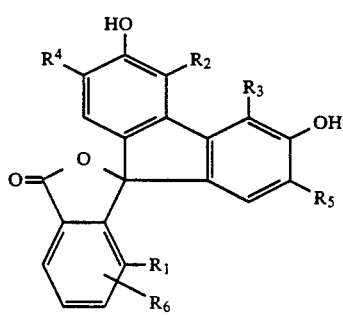

or

-continued

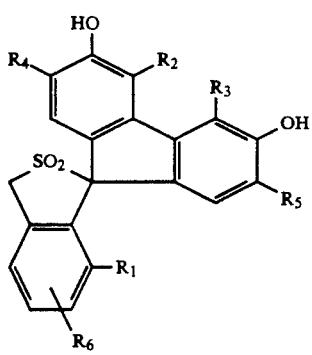

wherein $R_1$ is substituted or unsubstituted alkyl, aryl or alkoxy, or together with $R_6$ in the 6'-position of the phthalide moiety represents the atoms necessary to complete a substitute or unsubstituted 5- or 6-membered carbocyclic ring.

14. A compound as defined in claim 13 wherein $R_2$ and $R_3$ are each hydrogen.

15. A compound as defined in claim 13 wherein $R_1$ is methyl and $R_2$, $R_3$, $R_4$, $R_5$ and $R_6$ are each hydrogen.

16. A compound as defined in claim 13 wherein $R_1$ and $R_6$ are each methoxy and $R_2$, $R_3$, $R_4$ and $R_5$ are each hydrogen.

17. A compound as defined in claim 14 which is represented by the formula

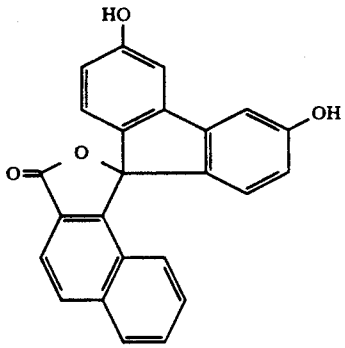

18. A compound as defined in claim 14 wherein $R_1$ and $R_6$ are each methyl and $R_4$ and $R_5$ are each carboxy.

* * * * *